US008072009B2

(12) United States Patent
Krauss

(10) Patent No.: US 8,072,009 B2
(45) Date of Patent: Dec. 6, 2011

(54) GAS SENSOR HAVING A FIELD-EFFECT TRANSISTOR

(75) Inventor: Andreas Krauss, Tuebingen (DE)

(73) Assignee: Robert Bosch GmbH, Stuttgart (DE)

( * ) Notice: Subject to any disclaimer, the term of this patent is extended or adjusted under 35 U.S.C. 154(b) by 50 days.

(21) Appl. No.: 12/635,224

(22) Filed: Dec. 10, 2009

(65) Prior Publication Data
US 2010/0148222 A1 Jun. 17, 2010

(30) Foreign Application Priority Data
Dec. 16, 2008 (DE) .......................... 10 2008 054 752

(51) Int. Cl.
*G01N 27/403* (2006.01)
(52) U.S. Cl. .................... 257/253; 257/3; 257/E31.053; 257/E29.255

(58) Field of Classification Search ............. 257/253, 257/3, E31.053, E29.255
See application file for complete search history.

(56) References Cited

U.S. PATENT DOCUMENTS

| 5,698,771 A * | 12/1997 | Shields et al. .......... 73/31.05 |
| 2004/0255669 A1* | 12/2004 | LaBarge et al. ......... 73/304 R |
| 2007/0132043 A1* | 6/2007 | Bradley et al. ........... 257/414 |

FOREIGN PATENT DOCUMENTS

| DE | 10 2005 008 051 | 8/2006 |
| DE | 102005033639 A1 * | 1/2007 |

* cited by examiner

*Primary Examiner* — Tu-Tu Ho
(74) *Attorney, Agent, or Firm* — Kenyon & Kenyon LLP

(57) ABSTRACT

A gas sensor having a field-effect transistor for detecting gases or gas mixtures is provided. The gas sensor includes a substrate having a source, drain and gate region, a gas-sensitive layer being applied on the gate region. A porous adhesive agent is provided for the adhesion of the gas-sensitive layer in the gate region.

12 Claims, 1 Drawing Sheet

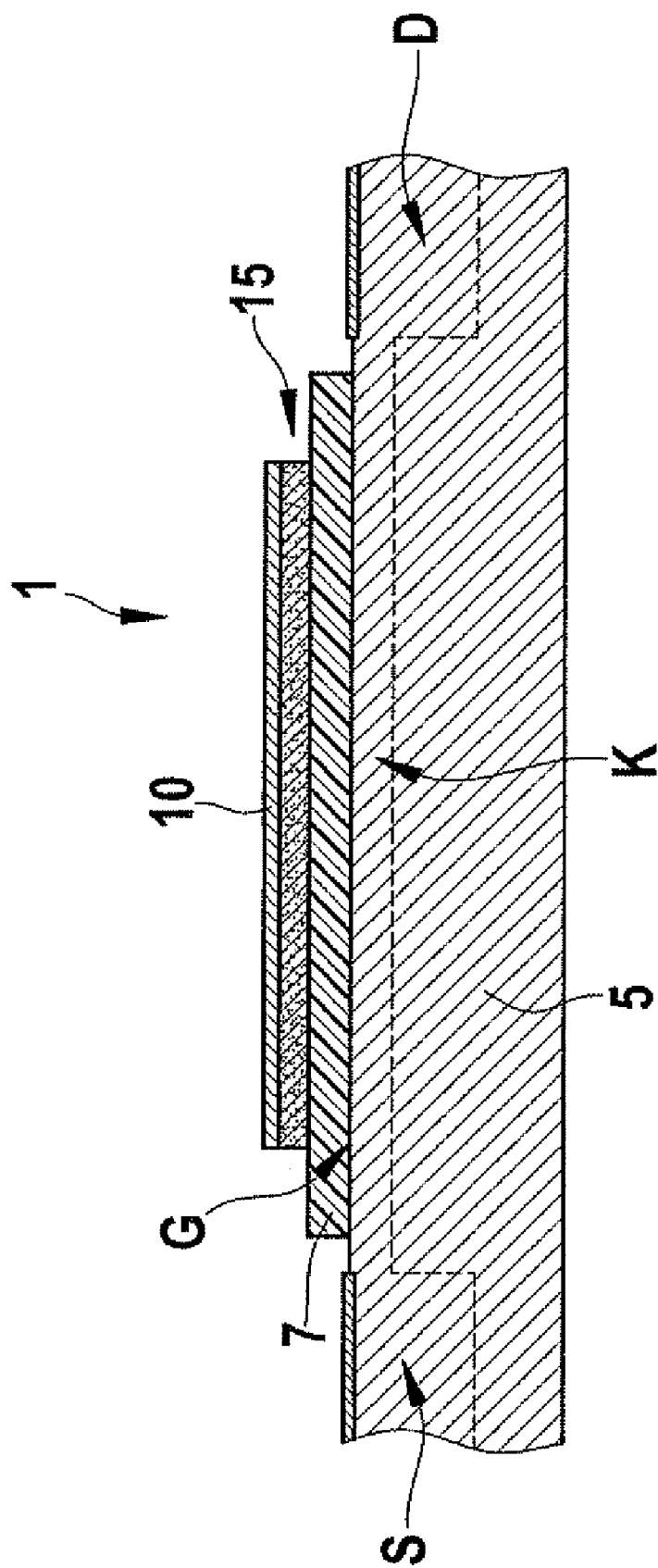

GAS SENSOR HAVING A FIELD-EFFECT TRANSISTOR

FIELD OF THE INVENTION

The present invention relates to a gas sensor having a field-effect transistor (FET) for detecting gases or gas mixtures.

BACKGROUND INFORMATION

Gas sensors having field-effect transistors are generally known. Their basic measuring principle is based on a diffusion of the gases to be detected into a gas-sensitive layer, which induces a change in the potential at the FET. A field-effect transistor having a source (S), drain (D) and gate (G) region is situated on a substrate, a gas-sensitive layer being applied on the gate (G) region. If the FET-based gas sensor (FET gas sensor) is exposed to a gas or a gas mixture, the gas or gas mixture to be detected diffuses into the gas-sensitive layer and in so doing, produces or changes the potential at the boundary surface to the channel region (C) between the source (S) and the drain (D) regions. This change in potential is able to be tapped as a measuring signal via a current or voltage change. Various modifications or further developments based on this basic principle are known as well.

The sensitive layer is usually separated from the gate (G) region by an intermediate layer disposed in-between. On the one hand, this protects the gate (G) region from harmful gas actions. On the other hand, the sensitive layer, which usually is electrically conductive in order to allow for the adjustment of a defined potential at the gate (G) region, is electrically insulated from the channel region (C) of the FET. That is to say, the intermediate layer is used as a protective layer for the gate (G) region and simultaneously as an insulation layer.

In German Patent Application No. DE 10 2005 008 051, for example, a gas-sensitive FET and a method for its operation are described, the sensitive layer having a porous design with open pores and any desired thickness and being directly applied on an insulation of a FET while avoiding an air gap. The sensitive layer is situated directly above the channel region of the FET or cooperates indirectly with the FET via a potential-free floating gate electrode.

In order to be able to perform the function of a chemical protective and electric insulation layer in a reliable manner, the separation layer is formed by a chemically inert, electrically insulating, closed and compact layer, if possible. The usual materials for this purpose are, for example, thermal oxides, LPCVD (low pressure chemical vapor deposition) oxides or also LPCVD nitrides. These layers have little surface roughness. This results in modest adhesion of the sensitive layer to the separation layer.

On the other hand, excellent adhesion of the sensitive layer to the FET is an important prerequisite for a reliable and long-term functionality of the gas sensor. For the sensors are often used in a measuring environment that exposes the sensitive layers to high mechanical or chemical stresses. One pertinent example is the use of a gas sensor for the $NO_x$ detection in the exhaust tract of an internal combustion engine. Mechanical stressing may be caused by, for example, strong vibrations, a very dynamic gas flow, or also by temperature-related freezing. Chemical stressing may be caused by exhaust gas or moisture in the measuring environment, for instance.

Consequently, there is demand for a gas sensor having a field-effect transistor in which the sensitive layer has improved adhesion to the gate (G) region of the sensor compared to current FET gas sensors known from the related art.

SUMMARY OF THE INVENTION

The FET gas sensor according to the present invention has the advantage of ensuring improved adhesion for the sensitive layer. The improved adhesion then permits a reliable and long-term use of the FET gas sensor even in a difficult environment with great stresses on the sensitive layer.

This advantageous effect is obtained by a porous material, which is provided as an adhesive agent.

The present invention requires no complicated modifications in the manufacturing process of the FET gas sensor; instead, the porous material provided according to the present invention is able to be integrated in the existing manufacturing process in a simple and suitable manner.

Furthermore, it is advantageous that it is also possible to select for the porous material an initially non-porous, i.e., compact, material in the manufacturing process of the FET sensor. The porosification of the material is able to be achieved during the manufacturing process of the FET sensor. When using a material that is initially compact following the application, then the material may be rendered porous especially in a spatially resolved manner, e.g., in an electrochemical or chemical reaction using a photo mask, or in the form of a photo-induced reaction with selective exposure. This makes it possible to represent regions which can accommodate a subsequent coating in a spatially dissolved manner.

BRIEF DESCRIPTION OF THE DRAWING

FIG. 1 shows an exemplary embodiment of the FET gas sensor according to the present invention, in cross-section.

DETAILED DESCRIPTION

A first exemplary embodiment of the gas sensor according to the present invention is shown in FIG. 1. In principle, gas sensor 1 having a field-effect transistor (FET) for detecting gases or gas mixtures has a substrate 5 which includes a source (S), drain (D) and gate (G) region, a gas-sensitive layer 10 being situated on the gate (G) region. In addition, a porous adhesive agent 15 for the adhesion of gas-sensitive layer 10 to gate (G) region is provided according to the present invention.

The pores of adhesive agent 15 advantageously provide the possibility for a deeper diffusion of sensitive layer 10 into the material of adhesive agent 15. The cavities of adhesive agent 15 may be filled with material of the sensitive layer, either completely or also at least partially. The sensitive layer is practically permanently anchored within adhesive agent 15. The porous characteristic of adhesive agent 15 thus produces a strong fixation between gas-sensitive layer 10 and adhesive agent 15.

It is preferred if porous adhesive agent 15 is disposed as an intermediate layer between the gate (G) region and gas-sensitive layer 10.

Porous adhesive agent 15 may have an electrically insulating characteristic. In such a case adhesive agent 15 also acts as electric insulation between the channel region (C) and sensitive layer 10. It is then possible to dispense with a separate insulation layer.

As an alternative, however, porous adhesive agent 15 may have an electrically conductive characteristic. In such a case it is advantageously also possible to apply sensitive layers that are not contiguous, i.e., unconnected layers, on the gate (G) region. These are then able to be contacted via electrically conductive adhesive agent 15.

Furthermore, if required, an electric insulation layer 7 may be situated between porous adhesive agent 15 and the gate (G) region. This may be necessary, for instance, when adhesive agent 15 is electrically conductive, as described earlier. In the case of an electrically insulating adhesive agent 15 as well, a protective layer in the form of an insulation layer 7 may constitute a suitable measure for protecting the gate (G) region, for instance from the direct effect of the gas, or for enhancing the electric insulation in addition to electrically insulating adhesive agent 15.

In one especially preferred specific embodiment of the present invention, porous adhesive agent 15 is formed by porous silicon carbide (SiC). On the one hand, this material selection provides a chemically inert semiconductor material, so that any undesired effect of the ambient gases on adhesive agent 15 made of porous SiC is able to be avoided. Sic is particularly suitable for use in a rough environment on account of its pronounced high chemical and thermal stability.

On the other hand, current technologies are advantageously available that allow reliable processing of the semiconductor material SiC. This ensures a controlled production of porous SiC. Furthermore, the production of an adhesive agent 15 on the gate (G) region is able to be integrated into an existing production process of an FET gas sensor without great outlay. Finally, via selective doping of the material, the electrical conductivity of the SiC is adjustable in a defined manner. This results in the basic freedom of design in the use of the SiC material as adhesive agent 15 with regard to whether adhesive agent 15 is to be available in electrically conductive or in insulating form.

Another suitable material for porous adhesive agent 15 is porous silicon (Si). In principle, the aforementioned advantages of SiC also hold true for Si, but compared to SiC, they apply only to a limited extent with regard to the chemical and thermal stability. However, a large spectrum of processing methods and perfected processes is available for Si as a central material in semiconductor technology.

In another, especially advantageous specific embodiment, the porosification of porous adhesive agent 15 has a gradient. That is to say, the degree of the porosification of adhesive agent 15 is not constant but instead varies within the layer along a spatial direction. It is suggested that the porosification of adhesive agent 15 increases in the direction facing away from substrate 5. For example, in a special case a continuous material is present in a lower region of adhesive agent 15, i.e., the region closest to channel region (C). That is to say, there is no porous material in this region at all. However, the porosification increases in the direction of the upper region, i.e., the region most remote from channel region (C). The porosification is then most pronounced on the outer surface of adhesive agent 15.

On the one hand, such a procedure advantageously ensures the most optimal, i.e., permanent, connection of adhesive agent 15 and the layer disposed underneath, channel region (C) or possibly an insulation layer 7. On the other hand, the high porosification in the upper region of adhesive agent 15 achieves sufficient diffusion of the gas-sensitive layer into adhesive agent 15, and thus its solid anchoring within adhesive agent 15.

Regardless of whether the porosification in adhesive agent 15 varies or not, gas-sensitive layer 10 may be applied to porous adhesive agent 15 or also intercalated therein. In the former case, gas-sensitive layer 10 projects beyond adhesive agent 15 in height, as illustrated in FIG. 1, while in the latter case, gas-sensitive layer 10 has been fully absorbed within the porous material of adhesive agent 15, so that gas-sensitive layer 10 does not project beyond adhesive agent 15 (not shown in the FIGURE). In both cases, at least a portion of gas-sensitive layer 10 has diffused into the porous material of adhesive agent 15. This infused component of gas-sensitive layer 10 in the porous material of adhesive agent 15 is not illustrated explicitly in FIG. 1 for reasons of clarity of the drawing.

Besides, in all specific embodiments of the present invention the adhesion of gas-sensitive layer 10 at the gate (G) region may be more pronounced with the aid of a drying and/or sintering process.

Finally, it is stated that the present invention has shown to be especially useful if gas-sensitive layer 10 includes crystalline, especially nanocrystalline, metals.

What is claimed is:

1. A gas sensor having a field-effect transistor for detecting gases or gas mixtures, comprising:
a substrate having a source region, a drain region and a gate region;
a gas-sensitive layer situated on the gate region; and
a porous adhesive agent situated in the gate region for an adhesion of the gas-sensitive layer;
wherein the porous adhesive agent is an intermediate layer between the gate region of the substrate and the gas-sensitive layer, and wherein the gas-sensitive layer is intercalated in the porous adhesive agent.

2. The gas sensor according to claim 1, wherein the porous adhesive agent has an electrically insulating characteristic.

3. The gas sensor according to claim 1, wherein the porous adhesive agent has an electrically conductive characteristic.

4. The gas sensor according to claim 1, further comprising an electric insulation layer situated between the porous adhesive agent and the gate region.

5. The gas sensor according to claim 1, wherein the porous adhesive agent is formed by porous silicon carbide.

6. The gas sensor according to claim 1, wherein the porous adhesive agent is formed by porous silicon.

7. The gas sensor according to claim 1, wherein the gas-sensitive layer is applied in the porous adhesive agent.

8. The gas sensor according to claim 1, wherein the adhesion of the gas-sensitive layer to the gate region is enhanced with the aid of at least one of a drying process and a sintering process.

9. The gas sensor according to claim 1, wherein the gas-sensitive layer includes crystalline metals.

10. The gas sensor according to claim 1, wherein the gas-sensitive layer includes nanocrystalline metals.

11. A gas sensor having a field-effect transistor for detecting gases or gas mixtures, comprising:
a substrate having a source region, a drain region and a gate region;
a gas-sensitive layer situated on the gate region; and
a porous adhesive agent situated in the gate region for an adhesion of the gas-sensitive layer;
wherein the porous adhesive agent has a porosification with a gradient.

12. The gas sensor according to claim 11, wherein an intensity of the porosification of the adhesive agent increases in a direction facing away from the substrate.

* * * * *